US007745976B2

(12) United States Patent
Cerofolini (10) Patent No.: US 7,745,976 B2
(45) Date of Patent: Jun. 29, 2010

(54) ULTRASOUND PROBE, PARTICULARLY FOR DIAGNOSTIC IMAGING

(75) Inventor: Marino Cerofolini, Subbiano (IT)

(73) Assignee: Esaote, S.p.A., Milan (IT)

( * ) Notice: Subject to any disclaimer, the term of this patent is extended or adjusted under 35 U.S.C. 154(b) by 1167 days.

(21) Appl. No.: 11/334,635

(22) Filed: Jan. 18, 2006

(65) Prior Publication Data
US 2006/0184033 A1    Aug. 17, 2006

(30) Foreign Application Priority Data
Jan. 18, 2005   (EP)   ................... 05100284

(51) Int. Cl.
*H01L 41/08* (2006.01)
(52) U.S. Cl. ...................................... 310/334
(58) Field of Classification Search .......... 310/317, 310/319, 334
See application file for complete search history.

(56) References Cited
U.S. PATENT DOCUMENTS

| 3,537,669 | A | * | 11/1970 | Modesti | ..................... 244/23 C |
| 3,952,216 | A |   | 4/1976  | Madison et al. | |
| 4,783,888 | A | * | 11/1988 | Fujii et al. | ................. 29/25.35 |
| 5,115,809 | A |   | 5/1992  | Saitoh et al. | |
| 5,175,709 | A | * | 12/1992 | Slayton et al. | ................. 367/90 |
| 5,724,976 | A |   | 3/1998  | Mine et al. | |
| 5,974,884 | A |   | 11/1999 | Sano et al. | |
| 6,645,145 | B1 |  | 11/2003 | Dreschel et al. | |
| 6,736,779 | B1 | * | 5/2004 | Sano et al. | ................... 600/447 |
| 6,806,623 | B2 | * | 10/2004 | Petersen et al. | ............. 310/334 |
| 7,109,642 | B2 | * | 9/2006  | Scott | ........................... 310/334 |
| 7,459,836 | B2 | * | 12/2008 | Scott | ........................... 310/334 |
| 2007/0016058 | A1 | * | 1/2007 | Kerwin | ....................... 600/459 |

FOREIGN PATENT DOCUMENTS

| JP | 11 155863 | 6/1999 |
| JP | 2000139907 | 10/2000 |
| WO | WO 94/13411 | 6/1994 |

* cited by examiner

Primary Examiner—Thomas M Dougherty
(74) Attorney, Agent, or Firm—Woodard, Emhardt, Moriarty, McNett & Henry LLP (57) ABSTRACT An ultrasound probe particularly for diagnostic purposes includes a first array of ultrasound transducers that generate ultrasound waves by electric excitation and transforming ultrasound waves impinging on them into electric signals. Each transducer is provided with contact electrodes which are connected respectively to a ground potential and to electric signals feeding lines. The first array of transducers includes emitting transducers and is intended only for generating and transmitting ultrasound waves, while a second array of transducers is provided over the first array of emitting transducer and includes receiving transducers for generating the electric receipt signals. The second array of transducers is formed of a material having piezoelectric behavior.

22 Claims, 7 Drawing Sheets

ULTRASOUND PROBE, PARTICULARLY FOR DIAGNOSTIC IMAGING

CROSS-REFERENCE TO RELATED APPLICATION

The present application claims the benefit of European Patent Application Ser. No. 05100284.8, filed on Jan. 18, 2005, which is hereby incorporated by reference in its entirety.

BACKGROUND

The invention relates to an ultrasound probe particularly for diagnostic purposes.

A typical structure of an ultrasound probe, particularly for an ultrasound probes used for ultrasound diagnostic imaging incorporates ultrasound transducers. These transducers are often piezoelectric elements, typically ceramic elements, which upon excitation with an electric potential are driven to oscillation of the ceramic crystal lattice, which generate mechanical waves in the frequency range of ultrasound acoustic waves. The frequency of the waves and the shape and spectral composition of the ultrasound waves generated depends on the frequency, shape and spectral composition of the electric excitation pulses.

Conversely, ultrasound transducers are capable of generating electric signals upon mechanical excitation of their crystal lattice by an impinging mechanical (e.g., acoustic) force or waves. The frequency range, shape and spectral composition of the generated electric signal depends on frequency range, shape and spectral composition of the impinging acoustic waves, for example.

The same transducer array may be used alternatively as a receiving and as an emitting device for converting electric excitation pulses into acoustic pulses and acoustic excitation pulses into electric pulses.

In a typical ultrasound probe, a transmission and receipt switch is provided which after each excitation by electric signals the emission of acoustic waves turns the conductors of the electric signals associated with the transducers to a receipt section of an ultrasound system by which the electric signals generated by the impinging reflected acoustic waves are elaborated or analyzed in order to extract information such as, for example, image data. Due to the fact that the probe is connected by means of a cable having a certain length and having a high capacity with respect to the power of the electric signals generated by the transducers upon acoustic excitation. It would be desirable to have each transducer further connected to a preamplifier, or just a signal follower, which enhances the signal power in order to allow its conduction through the cable, thus improving the sensitivity and/or the bandwidth.

The problem of the power of the electric signal does not arise for the excitation signals sent to the transducers, since a dedicated section generates these signals and the power of the signals can be adjusted easily at a level ensuring the correct transmission to the transducers.

Nevertheless in using the same transducers for emission of ultrasound waves and for receipt of ultrasound waves causes some problems for the preamplifiers that have to be rather complex, since, due to the fact that the same conductor line is used for transmitting the excitation signals to the transducers and for collecting the receipt signals generated by impinging reflected ultrasound waves from the transducers, the preamplifiers need a decoupling section to avoid shortcuts during transmission of the excitation signals to the transducers.

These decoupling circuits need several components which increase the physical dimensions of the preamplifier in a dramatic way. The dimensional part of the preamplifier due to the decoupling circuits can be even greater that the one needed for the preamplifier itself. Furthermore the decoupling circuits give rise to major costs due to a more complicated structure of the preamplifier and to higher costs for miniaturization by means of the actual techniques of integration.

On the other hand the use of the same array of transducers for generating and emitting the ultrasound transmission waves and for receiving the reflected ultrasound waves reduces the dimensions and the weight of the probe itself which, particularly for diagnostic applications, is very important due to the fact that the probe is manipulated mostly by hand.

Providing two different array of transducers, one of which is only dedicated to generating the ultrasound transmission waves and the second of which is only dedicated to receiving the reflected or impinging ultrasound waves, would overcome the above mentioned problems. On the other hand, considering matching of the acoustic impedance, acoustic separation and electric separation of the two transducer arrays, this solution would lead to a considerable increase of the dimensions and of the weight of the probe.

Another possible way of solving the above problem would consist in using only part of the transducer of the array for generating and transmitting the ultrasound waves and part of the transducers of the array only for receiving the impinging or reflected ultrasound waves. This solution also solves the above mentioned problems and no increase in the overall dimensions of the probe would be caused by this solution. On the other hand, using only part of the transducers for transmitting and for receiving the ultrasound waves would cause a reduction of the quality of the data extracted from the reflected ultrasound beams, such as power of the reflected ultrasound waves and image definition.

A third aspect has further to be considered which has a particular relevance in ultrasound diagnostic imaging and which is related to the matching layers. These layers must match the acoustic impedance of the transducers with the one of the body under examination but the matching must be achieved without reducing the bandwidth of the probe either for the case of the transmission of the ultrasound waves and in the case of the receipt of the reflected ultrasound waves. This aspect is relevant in the case of two different arrays of transducers being used independently for transmission and for receipt of the ultrasound waves. Thus using two separate arrays of transducers laid one over the other would cause problems for matching the acoustic impedance and furthermore for ensuring at the same time the expected or needed pass bandwidth.

SUMMARY

The object of the present disclosure is to provide for an improved ultrasound waves transmitting and receiving probe that overcomes the above mentioned problems of the known probes by providing separate ultrasound waves transmission and receipt array of transducers without taking into account an excessive dimensional increase of the probe and ensuring an optimum matching of the acoustic impedance with a sufficient bandwidth.

At the same time the invention has the aim to provide an ultrasound transmitting and receiving probe having a simplified and dimensionally limited array of preamplifiers for the electric receipt signals generated by the transducers of the array dedicated to the receipt of the reflected or impinging ultrasound waves.

The invention achieves the above mentioned aims by means of an ultrasound probe in which a first array of transducers is intended only for generating and transmitting the ultrasound waves and a second array of transducers is laid over the first transducer array which is intended only for generating the electric signals due to acoustic excitation of the transducers of the second transducer array by means of the impinging or of the reflected ultrasound waves. The second array of transducers is formed of a material having piezoelectric behaviour and an acoustic impedance intermediate to that of the first array of transducers and of the body under examination, forming at the same time one of the matching layers covering the first array of transducers on the side thereof oriented in the direction of propagation of the ultrasound waves emitted by the said first array of transducers. The second array of transducers comprises transducers made of Polivinilchloride PVC or polivinilidilenefluoride PVDF.

Each transducer is coupled to two electrodes: one for collecting the electric signal generated due to acoustic excitation of the transducer by means of the reflected beams and the other connected to ground potential.

Typically, transducers of an array are mechanically integrated in a layered pack which is formed by the transducers themselves which are spaced one from the other, with the spaces between the transducers being filled with a filling and bonding material.

The transducer array in the form of a pack can include also the electrodes which are formed by an array of electrodes, each electrode of the array coinciding with a surface of one transducer and the array of electrodes being in the form of a layer.

Also typically the pack is formed by a first electric contact layer consisting of a first array of contact electrodes on which a layer of coinciding transducers is provided, and a second layer of contact electrodes comprising an array of second electrodes where the second contact electrodes are coincident with the transducers and where the second layer is laid on the transducer array, with the filling material being provided for bonding the array layers of transducers and contact electrodes in a pack.

Each contact electrode of each array of contact electrodes is separately connected to a wire for connecting the electrode to ground potential or to an electric excitation signal generating unit or to an electric signal receiving unit.

This construction is of typical construction for an array of ultrasound transducers and is identical for the first and for the second array of transducers respectively dedicated to emitting the ultrasound waves and to receiving the reflected or impinging ultrasound waves.

Different ways of producing the pack of transducers with the contact electrodes are used and any of these ways can be used in combination with the present disclosure.

Typically the contact electrodes associated with the transducers are layered on two opposite sides of the transducers, for example, by vapour deposition or by plasma deposition. The conductors connecting the signal transmitting or receiving lines can be formed by conducing tracks provided on a substrate in the form of a printed circuit or the like.

The conductor for connecting the ground electrodes of the transducers to ground potential can consist simply by a continuous layer or thin plate of conductive material.

The electrodes can be applied to the transducers in several ways, as for example, by bonding to two opposed surfaces of a transducer having the form of a small block a conducting sheet, or depositing a conducting layer on the surfaces of the transducers by means of vaporization or by means of plasma deposition or by means of other known techniques.

Figure 1:
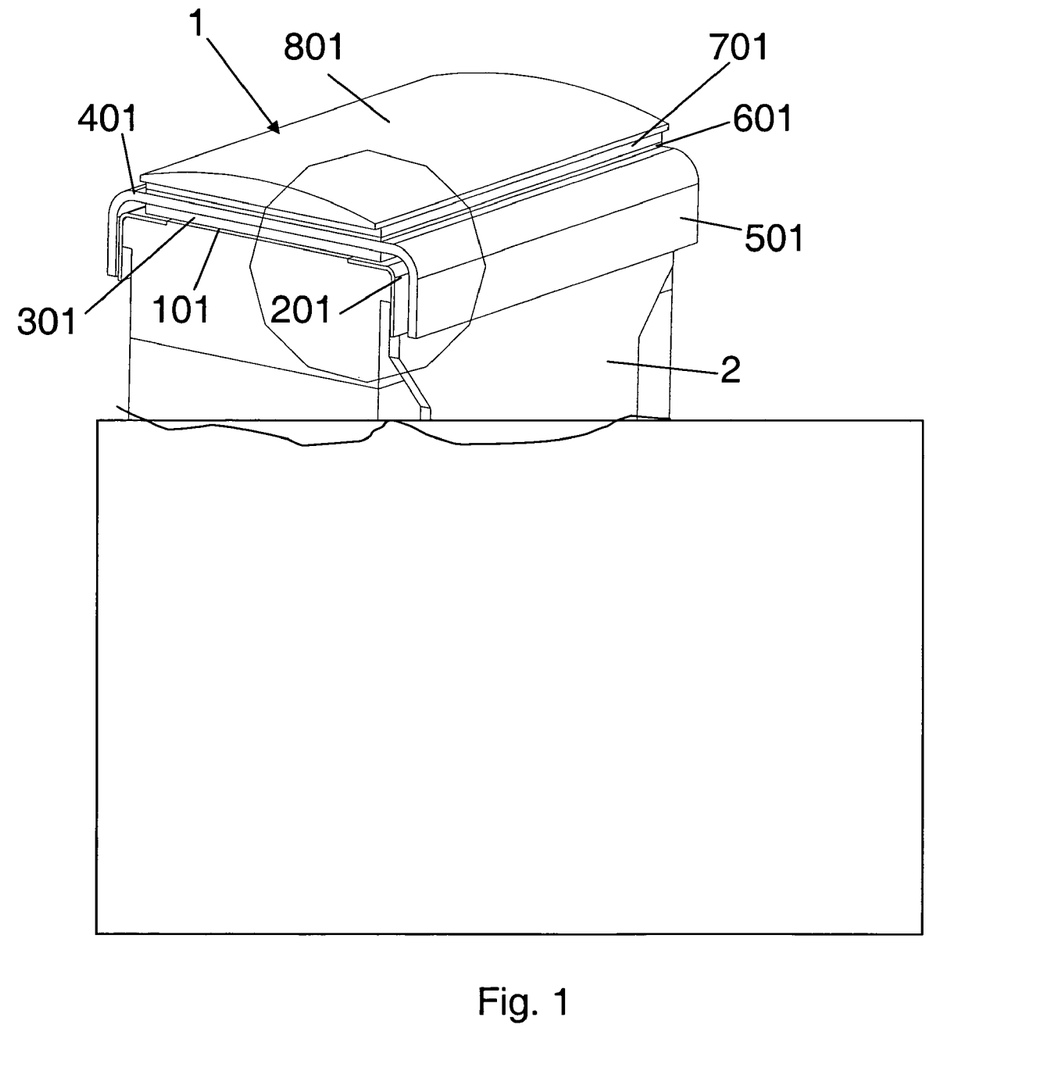
FIG. 1 illustrates a perspective view of the construction of an ultrasound emitting and transmitting head of a conventional probe according to the state of the art.
Figure 2:
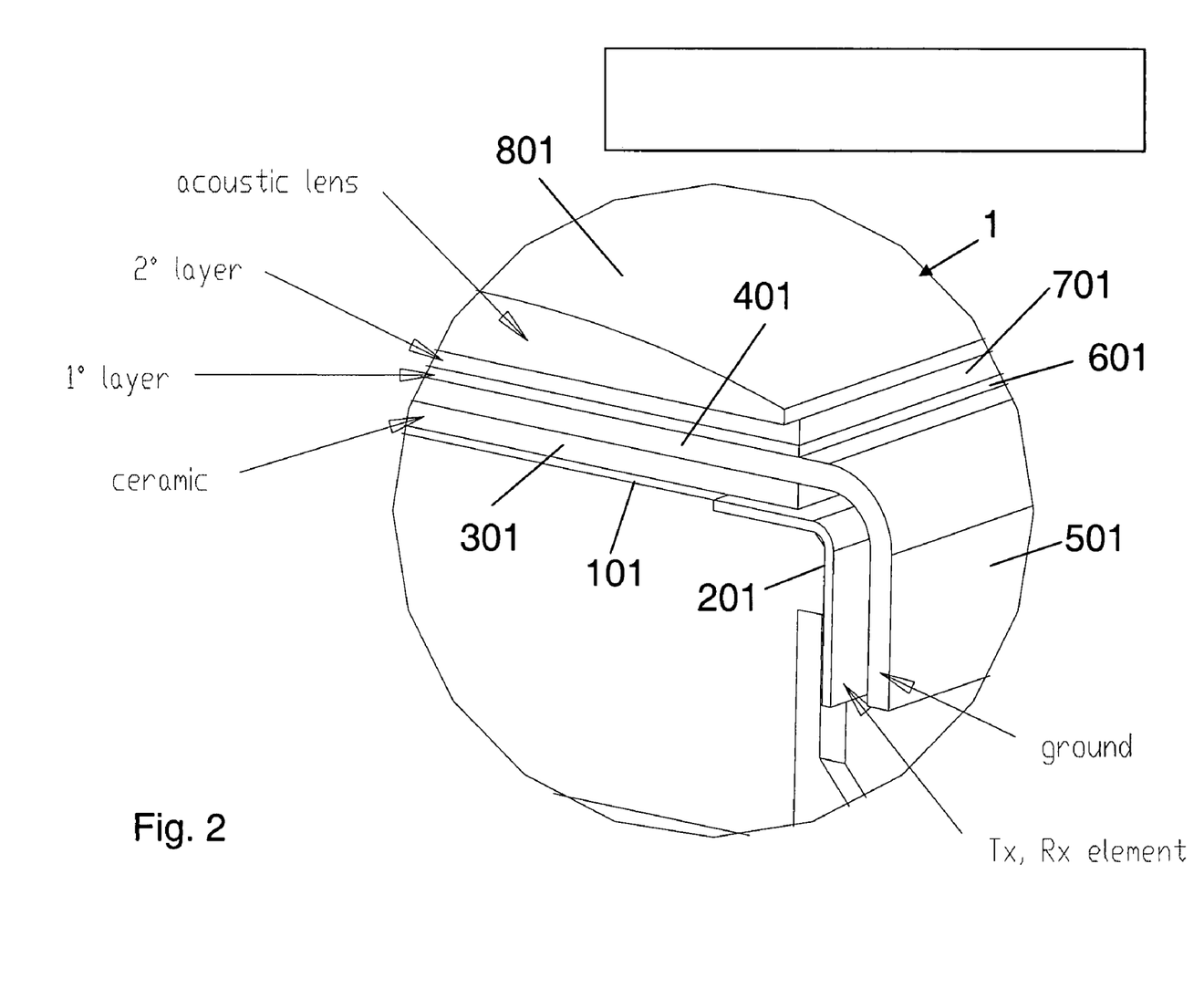
FIG. 2 illustrates an enlarged view of the probe head according to FIG. 1.
Figure 3:
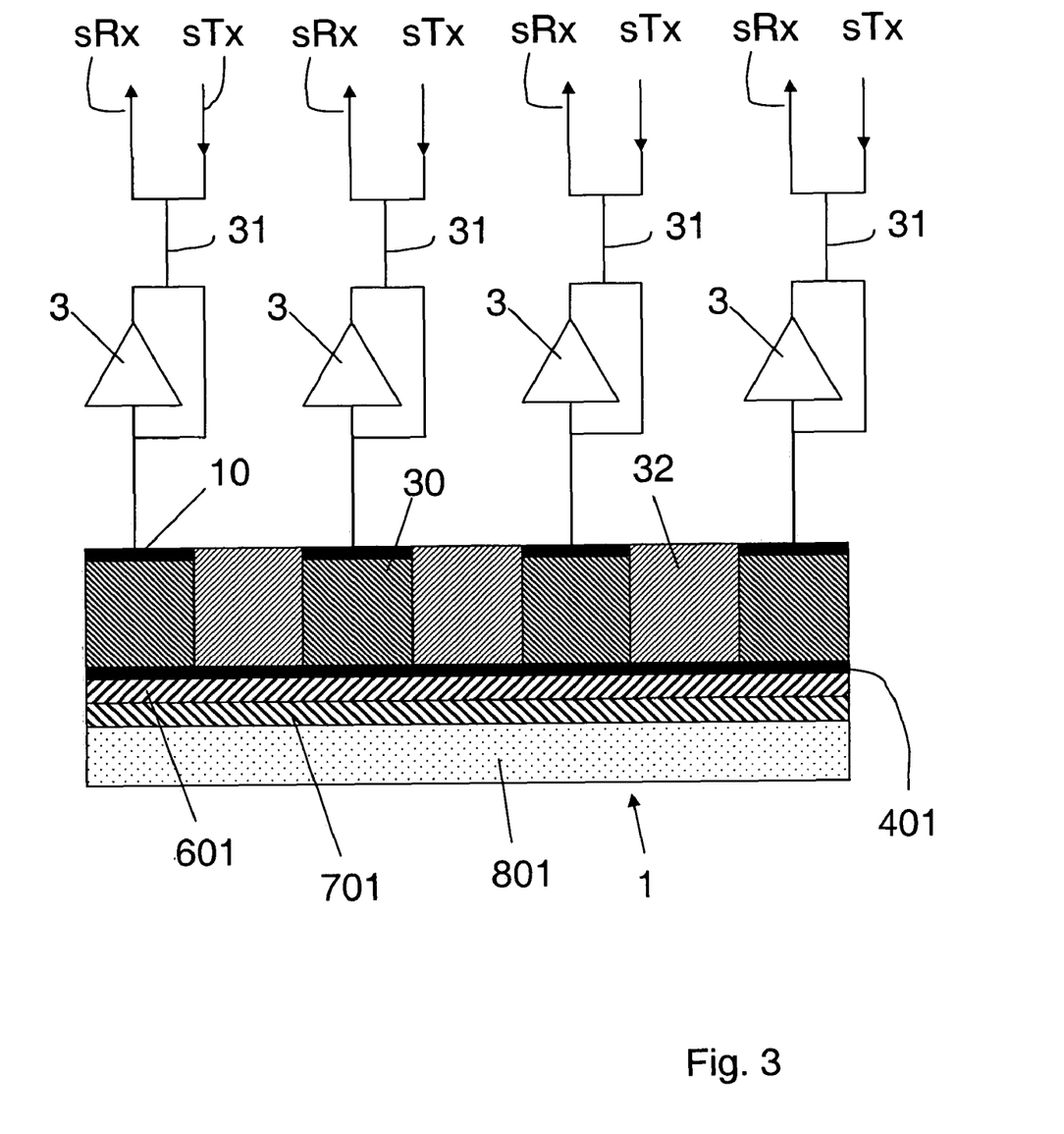
FIG. 3 illustrates a schematic view of the principle according to which the probe head of FIGS. 1 and 2 is constructed.

In an ultrasound probe according to the actual technique as illustrated in FIGS. 1 to 3, where the array of transducers is typically of ceramic and having the form of a layer there is provided a front surface and a rear surface, the front surface being the one from which the ultrasound waves are emitted or the one oriented forward according to the ultrasound emission end of a probe. The array of transducer is placed between a first layer formed by the array of contact electrodes for transmitting the electric excitation signals to the transducers and for receiving the electric signals generated by the transducers due to acoustic excitation, and a layer of conducting material forming the ground electrodes of the transducers, two further layers being provided placed on the conducting layer forming the ground electrodes which layers are a first and a second matching layer having a different acoustic impedance relative to the transducers and to the body under examination and relative one to the other in order to progressively vary the acoustic impedance along the path of the emitted waves from the acoustic impedance of the transducers to the acoustic impedance of the body under examination. An acoustic lens may be laid on the second matching layer.

In this case the present disclosure provides an improved probe wherein the second matching layer is made by a piezoelectric material and is formed by an array of elements having the function of ultrasound transducers. A layer made by an array of contact electrodes, each one coinciding and in electric contact with one of the piezoelectric elements, is provided between the said second matching layer and the first matching layer and a layer of conducting material forming the ground electrode is positioned between the said second matching layer and the acoustic lens and being in electric contact with the piezoelectric elements forming the second matching layer.

In this configuration, the first array of transducers of ceramic material is dedicated to emit the ultrasound which passes the first and second matching layer as in conventional probes, while the second matching layer formed by an array of piezoelectric elements is dedicated to generate the electric signals corresponding to the acoustic excitation of the piezoelectric elements of the second layer by the reflected or the impinging ultrasound waves.

Because of the fact that the function of the matching layers is important only relative to the ultrasound waves emitted by the probe and not for the reflected ultrasound waves impinging on the probe, the transducers for sensing the reflected beams are formed by the second matching layer and thus the ultrasound waves reach the transducers without having to pass the matching layers as in the conventional probe and therefore with no negative effects. On the contrary, this condition is a positive one since the ultrasound waves impinging on the transducers are not attenuated by the matching layers.

A preferred but not limiting embodiment of the probe according to the present disclosure comprises in order from the back side of the probe to the probe head from which the waves are emitted and at which the reflected waves are received a first layer made by an array of excitation contact electrodes which carry the excitation signals separately to each one of the transducers of a first array of ultrasound waves emission transducers laid over the said first layer of excitation contact electrodes carrying the excitation signals, a layer of electric conductive material laid on the first array of emission transducers and in electric contact with the emission transducers which layer of electric conductive material is connected to ground potential and forms the ground electrodes of the first array of emission transducers, a first matching layer made of a material having a first value of acoustic impedance between that of the first array of emission transducers and that of the body under examination in which the first matching layer is laid on the grounded layer of conductive material, a layer made by an array of receipt contact electrodes for carrying the receiving electric signals generated by a second array of receiving transducers due to acoustic excitation of the transducers of the second array of receiving transducers by the reflected or impinging ultrasound waves and where the layer of receipt contact electrodes is laid on the first matching layer, a second array of receiving transducers laid on the array of receipt contact electrodes for the receiving electric signals with each one of the transducers of the second array being in electric contact with one of the receipt contact electrodes of the array of receipt contact electrodes, and which second array of receiving transducers are made by a piezoelectric element having a value of acoustic impedance between the value of the acoustic impedance of the first matching layer and the value of the acoustic impedance of the body under examination, a layer of electric conductive material laid on the second array of receiving transducers being in electric contact with the receiving transducers and where the layer of electric conductive material is connected to ground potential and forms the ground electrodes of the second array of receiving transducers, and an acoustic lens laid over the grounded layer of electric conductive material.

Thus the first layer of transducers is only dedicated to the emission of ultrasound waves and the electrodes for carrying the electric excitation signals to the emission transducers are connected directly to a unit for generating such electric excitation signals.

The reflected ultrasound waves are sensed or received by the second array of receiving transducers and the electric receipt signals generated by the transducers upon acoustic excitation thereof are carried to a signal evaluation unit by means of the electric receipt signals electrodes of the second array of receiving transducers. At the same time the second array of transducers, or in combination the second array of transducers and the receipt contact electrodes for carrying the electric receipt signals and/or the ground electrodes, have the function of a second matching layer for the ultrasound waves emitted by the first array of emission electrodes.

According to a further feature of the present disclosure, the probe further comprises an array of preamplifiers to each one of which the receipt signal of a selected one of the transducers of the transducer array is fed by means of a signal feeding channel connecting the contact electrode of the selected transducer element with one of the preamplifiers of the array of preamplifiers.

Advantageously the preamplifiers may be in the form of integrated circuits mounted in an array disposition on a printed circuit board comprising conductive tracks, each one of which is a signal feeding channel connecting one of the integrated preamplifiers with the contact electrode of one selected transducer of the array of transducers.

In combination with a probe configuration according to the present disclosure and comprising an array of ultrasound wave emission transducers and a second array of ultrasound wave receiving transducers, the present invention suggests a receipt signal preamplifier having a very simple, cheap and small construction.

The preamplifier may comprise only a tension follower together with the typical resistors for correctly driving the tension follower and a decoupling circuit comprising two antiparallel diodes.

In a preferred embodiment, the tension follower consist in only a FET component.

The tension follower in the form of the FET and the typical resistors for correctly driving it and the decoupling circuit formed by the two anti-parallel diodes is realized preferably as an integrated circuit.

Due to the fact that the preamplifier and the associated decoupling circuit consist in very few electronic basic components, producing an integrated circuit comprising all these components is very cheap and the resulting integrated circuit has very small dimensions. This permits the production of very large arrays of preamplifiers which can be housed within the probe casing without requesting huge dimensions of the probe casing and thus maintaining the probe casing within dimensional limits which allows comfortable handling.

Also from the point of view of the weight, the probe according to the present disclosure can be easily maintained within acceptable weight limits concerning the comfort of handling the probe.

A probe according to the present disclosure can be so easily provided with arrays of transducers having a larger amount of transducers without having to take into account bigger dimensions and/or an increased weight of the probe casing and thus incurring in uncomfortable handling of the probe.

According to a further feature of the present disclosure, the probe comprises at least an array of receipt signal preamplifiers which are mounted on a printed circuit board, the printed circuit board being housed in the probe casing in a position which is transversal or substantially perpendicular to the surface of the array of transducers. The preamplifiers of the receipt signals can be also distributed on two arrays which are mounted each one on a side of the printed circuit board. Furthermore the preamplifiers can be distributed on two or more arrays each mounted on one circuit board. More than two arrays of preamplifiers can be mounted on both sides of two or more printed circuit boards, depending on the total number of the arrays.

If, for example, the preamplifiers are distributed on four arrays, two circuit boards can be provided with each one carrying two arrays, each one of the two arrays being mounted on a side of the printed circuit board.

In a probe of essentially conventional shape with a casing having an elongated form in a direction parallel to the direction of propagation of the emitted ultrasound waves and which casing forms a handle for holding the probe, the probe has two opposite ends in which one of which carries the arrays of transducers and from the other end a multi-channel cable departs for connecting the probe to an ultrasound system where one or more printed circuit boards carrying the array or the arrays of preamplifiers are positioned in the axial direction of the probe casing.

The printed circuit board or boards are preferably provided parallel to the sides of the probe casing which are parallel to the longer sides of the arrays of transducers and at the end facing the arrays of transducers the printed circuit board or boards can be provided with contact termination pins of conductive tracks provided on them or with a connector.

The array or the arrays of contact electrodes of the array or of the arrays of transducers are provided with a connector or with contact termination pins with the printed circuit board located along one or both of the said longer sides which contact termination pins or which connector is complementary to the one provided on the printed circuit board in order to generate at least an electric connection by soldering together coinciding contact pins or to generate a disengageable electric and mechanical connection by means of the connectors.

It is also possible to provide a printed circuit board also along each side of the probe casing parallel or tangential to three or to four or to more of the sides of the array of transducers, the arrays of contact electrodes being provided with a connector or with a contact termination pins on each of the sides.

As to the way of realizing the connectors or the contact termination pins of the array of electrodes several alternatives are known to skilled person from the state of the art and forms part of the ordinary knowledge or skill of the skilled person.

Relating to the construction of a conventional probe more details are disclosed in the documents U.S. Pat. Nos. 6,049,159 and 4,686,409.

The features of the present invention and the advantages deriving therefrom will appear more clearly form the following description of the preferred embodiments which are illustrated in the annexed drawings.

DESCRIPTION OF THE EMBODIMENTS

Referring to FIGS. 1 to 3, a conventional probe is illustrated therein.

The conventional probe comprises an ultrasound wave or signal emitting and receiving head 1 which has a front side from which the ultrasound waves are emitted in the direction against a body under examination or against another kind of target and on which the reflected ultrasound waves or signals or incoming ultrasound waves falls and are sensed. The ultrasound head has a back side which is opposite to the said front side and which is oriented towards the inside of a probe casing (not illustrated) and towards structure for supporting the probe head inside the probe casing.

The probe head comprises, in an order starting from the back side of the head towards the front side of the head, which order corresponds also to the direction of propagation of the emitted ultrasound waves, a first layer 101 formed by an array of contact electrodes. Each contact electrode of this layer 101 of contact electrodes has a separate electric connection line to a corresponding contact pin on a contact termination provided along at least one edge of the layer of contact electrodes and indicated as element 201.

On the layer formed by the array of contact electrodes, a layer 301, formed by an array of piezoelectric elements such as, for example, ceramic elements, is laid. Each one of the piezoelectric elements forms an emitting and receiving transducer. The single transducers are each one coincident and in electric contact with one of the contact electrodes of the layer 101. A further layer of conductive material 401 is laid on the layer 301 formed by the array of transducers, i.e. of piezoelectric elements, with the said conductive material of the layer 401 being in electric contact with each one of the said piezoelectric elements and being connected to ground potential by means of a contact termination 501. The layer 401 of conductive material forms the ground electrode of the transducers of the layer 301. The layer 401 may be in the form of an array of ground electrodes, but since the ground potential is common to every one of the transducers of the layer 301, there is no need to provide separate ground electrodes for each transducer, so that the layer 401 can be easily formed by a continuous layer of conductive material. On the other hand, the layer 101 of contact electrodes must be in the form of an array of at least electrically separated contact electrodes since each one of the contact electrodes has the function of feeding the electric excitation signal to its associated transducer and of collecting the electric receipt signal from its associated transducer when the transducer is mechanically excited by an impinging ultrasound wave.

On the grounded conductive layer 501 two further matching layers are provided which are indicated with numerals 601 and 701. These two layers have the function of adapting the acoustic impedance of the transducers to the acoustic impedance of the body under examination or of the target. Normally two layers are used in order to provide for a progressive stepwise adaptation which also maintains a sufficiently large bandwidth for the passing ultrasound waves.

Typically the first matching layer 601 is made of a material having an acoustic impedance of about 3 to 3.6 MRayl and the second matching layer 701 has an acoustic impedance of about 2 MRayl.

As a last element on the second matching layer 701 an acoustic lens 801 is placed which forms the interface between the head of the probe and the surface of a body under examination, or a target body.

The contact terminations 201 and 501 of the layer 101 formed by the array of contact electrodes, and of the layer 501 formed by the grounded conductive material, are electrically and mechanically connected to a printed circuit board 2 which is provided with the necessary conductive tracks which are connected to a probe connection cable (non illustrated) and which cable connects the probe with an ultrasound apparatus as for example an ultrasound imaging apparatus.

Typically as indicated in FIG. 3, the single piezoelectric elements indicated by numeral 30 forming the single transducers of the array of transducers of the layer 301 are connected by means of the contact electrodes 10 associated to the piezoelectric elements 30 by means of a common signal feeding line 31 for the electric exciting signal sTx of the piezoelectric element and for the electric receipt signal sRx generated by the piezoelectric elements to the corresponding units of the ultrasound apparatus, namely, respectively, an excitation signals generating unit and a receipt signals evaluating unit (not illustrated in detail).

Since the probe connection cable, which is typically a multi-channel cable, has a certain capacitance and the receipt signals generated by the transducers have insufficient power to overcome the capacitance of the probe connecting cable, in order to increase the sensitivity and/or the bandwidth it would be desirable to connect each sRx line to a corresponding preamplifier. The preamplifiers should be provided in the path of the receipt signals before reaching the probe connection cable and thus inside the probe casing.

However, due to the fact that a unique and common signal feeding line is provided for the excitation signals sTx and for the receipt signals sRx, the preamplifiers should be provided with complex decoupling circuits which avoid shortcuts during feeding of the electric excitation signals to the transducers. In fact, without such complex decoupling circuits, the output of any preamplifier would be short-cut with its input as the sRx and sTx signals share the common signal feeding line 31 as shown in FIG. 3. In order to reduce the dimensions of the single preamplifiers and of the associated decoupling circuits a high integration has to be carried out for these devices in order to reach a sufficiently small dimension that allows to fit the said devices all inside the probe casing. Thus costs of the preamplifiers are relatively high also considering the large number of these preamplifiers.

Referring to FIG. 3, there has to be noted that the single piezoelectric elements 30 of the array of transducers of layer 301 are normally bonded together at a distance by means of bonding material indicated with numeral 32 and which bonding material is normally an acoustic wave absorber so as to suppress the laterally emitted waves by the transducers. These technique is well known and common to all the arrays of transducers of ultrasound probes.

In the conventional probe according to FIGS. 1 to 3, the array of transducers forming layer 301 has at the same time the function of emitting and of receiving the ultrasound waves so that the signal feeding lines for the excitation signals and for the receipt signals are forcedly the same one since they are short circuited at least at the level of the contact electrodes.

Figure 4:
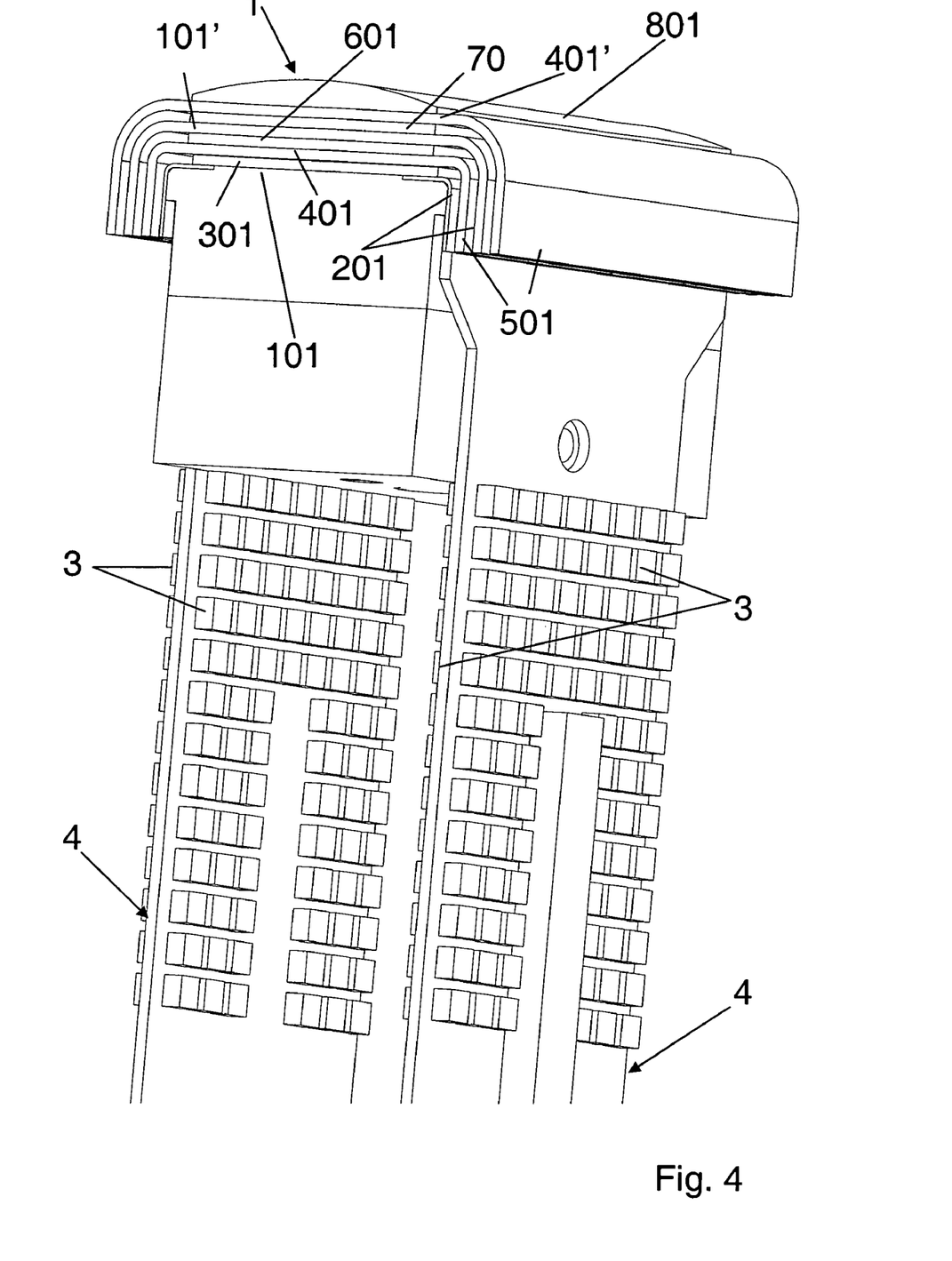
FIG. 4 illustrates a perspective view of the construction of an ultrasound emitting and receiving head of an ultrasound probe according to one embodiment of the disclosure.
Figure 5:
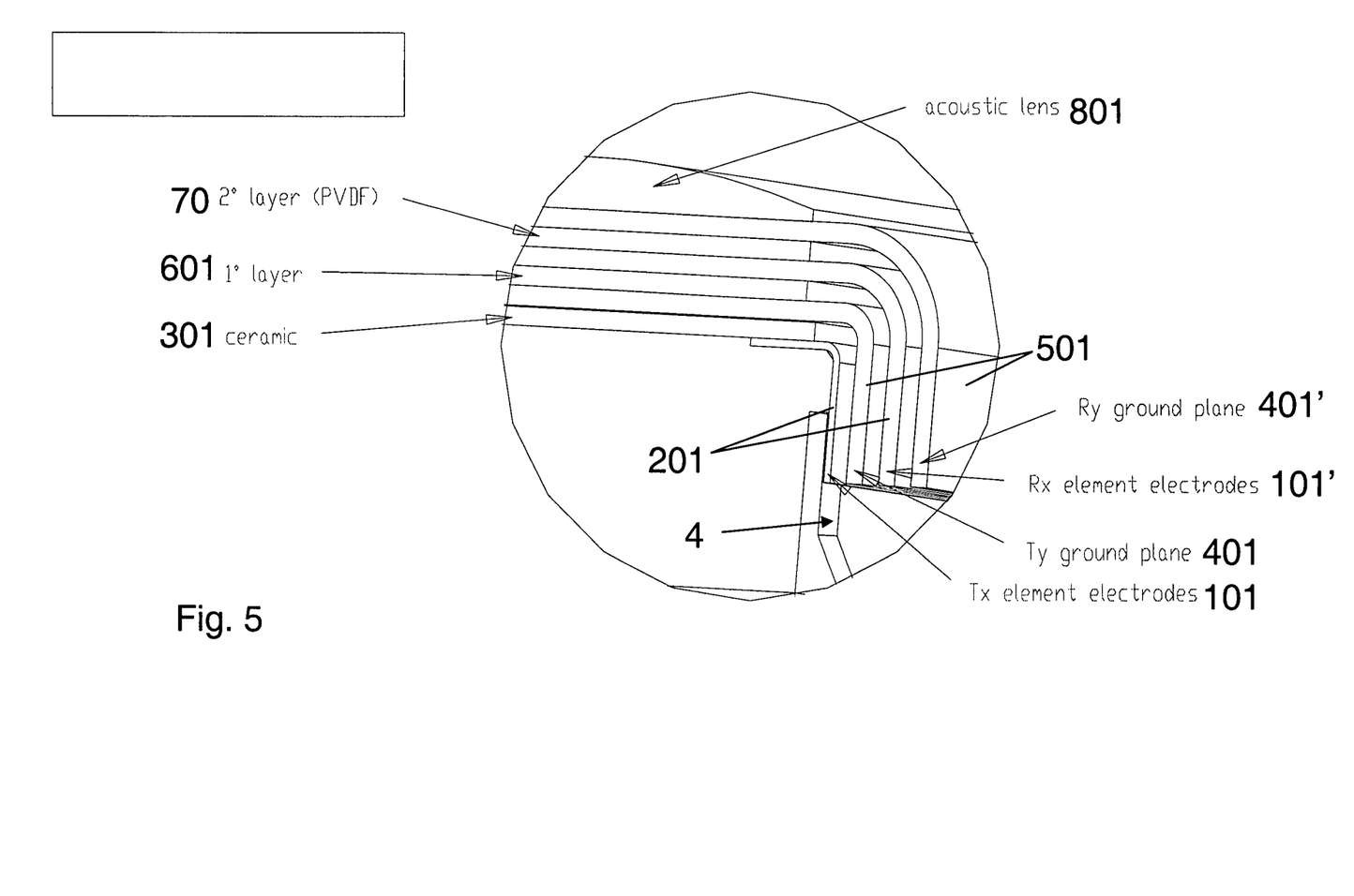
FIG. 5 is an enlarged view of a portion of the probe head according to FIG. 4.
Figure 6:
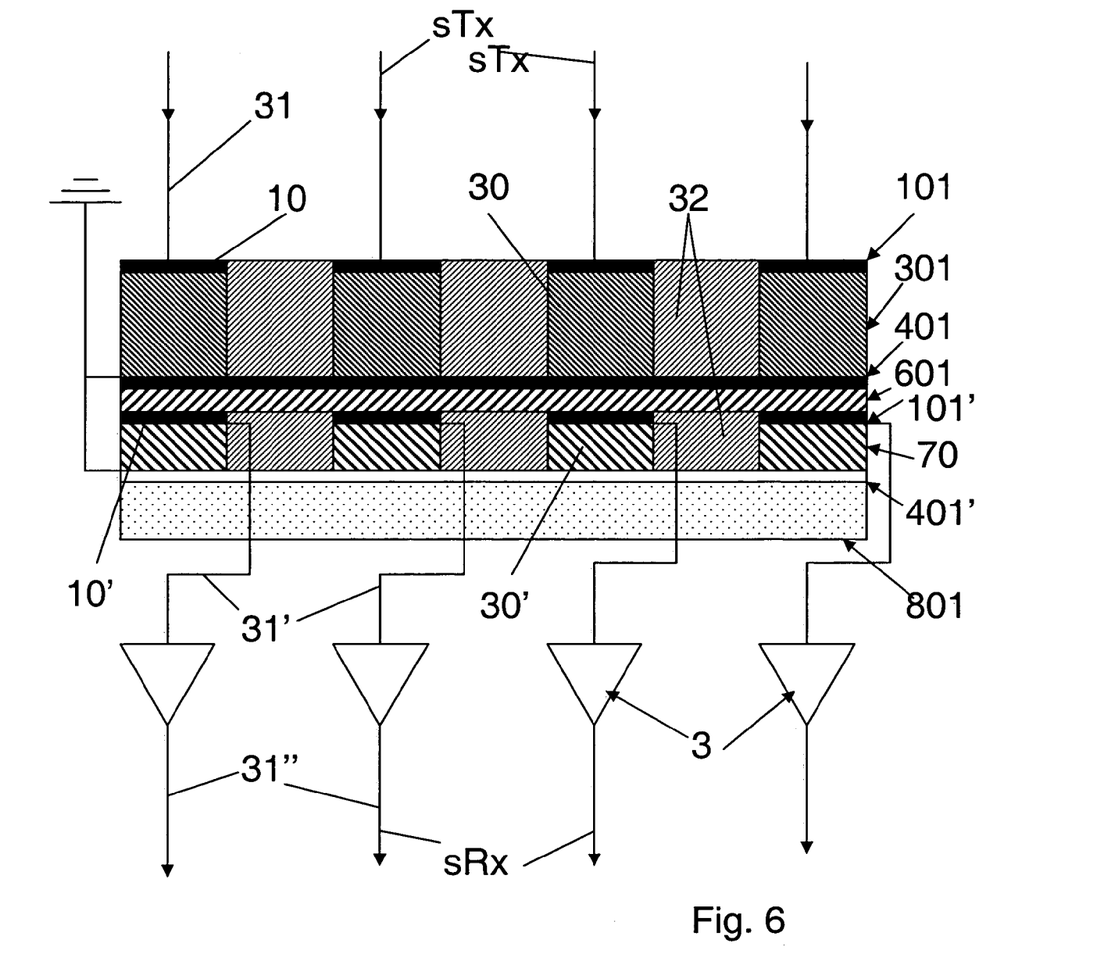
FIG. 6 is a schematic view of the principle of the construction of the probe head shown in FIGS. 4 and 5.

FIGS. 4, 5 and 6 illustrate a probe according to the present disclosure in which two separated array of transducers are provided, i.e., one solely for emitting the ultrasound waves and the other only for receiving ultrasound waves.

In the FIGS. 4 to 6 the same numerals are used for indicating similar parts or parts having the same function as in the FIGS. 1 to 3.

As it can be appreciated by simply comparing the structure of the probe head according to FIGS. 4 to 6 with the probe shown in FIG. 1 to 3, in the probe head according to FIGS. 4 to 6, the second matching layer 701 has been substituted by a layer 70 formed by an array of piezoelectric elements, i.e., of transducers. To this layer there are associated a dedicated further layer formed by an array of contact electrodes 101' and a dedicated further layer 401' formed by electric conductive material and forming the second electrode connected to ground potential of the second array of transducers of layer 70. Obviously once the layer 70 formed by the array of piezoelectric elements is provided, the two other layers formed by the array of contact elements and by the conductive material connected to ground potential become forcedly necessary if the array of transducers has to be used in order to be excited or to generate electric receipt signals.

According to the disclosure, the array of transducers of the first layer 301 are only used for emitting ultrasound waves, while the second array of transducers of layer 70 which are closer to the object under examination in the order of the layers are only used for generating the receipt signals, due to the mechanical excitation of the transducers by means of the impinging reflected ultrasound waves.

In order not to create a prejudice to the matching of the acoustic impedance needed for the emitted ultrasound waves, this second array of transducers of the layer 70 are made by a piezoelectric material having an acoustic impedance which is comparable to that of the second matching layers as disclosed above in relation to known probes.

A material having the values of acoustic resonance and a suitable piezoelectric behaviour is polyvinylchloride PVC or Polyvinyldilene fluoride PVDF.

Thus the probe according to the present disclosure provides a second layer 70 formed by an array of piezoelectric elements, i.e. transducers, which are made of one of the described materials, thus ensuring both the necessary matching for the ultrasound waves emitted by the first array of emitting transducers which is provided backwards of the layer 70 formed by the second array of receiving transducers and the necessary piezoelectric behaviour for ensuring that the mechanical excitation exercised by the impinging ultrasound waves is transformed in a corresponding electric signal.

For the array of receipt transducers no matching layer is necessary so that no further matching layer is needed between the array of transducers and the body under examination. Furthermore, due to the fact that the second array of receiving transducers is not covered by the matching layers as in a conventional probe head and that it is closer to the body under examination from which the impinging or reflected ultrasound waves arrives provides for higher intensity of the impinging waves.

Separating the transducers for emitting the ultrasound waves and for receiving the ultrasound waves has the advantage that separated feeding lines respectively for the excitation signals sTx and for the receipt signals sRx are possible. This is highlighted schematically in FIG. 6 where the feeding lines for the excitation signals sTx are indicated with numeral 31 and the feeding lines for the receipt signals sRx are indicated with numeral 31'.

Normally, however, for avoiding an increase of the separate conductors in the probe connection cable, the separated signal feeding lines 31, 31' relative to the same or to corresponding transducers of the two arrays of transducers are connected together to a common conductor of the multi-channel cable for connecting the probe to the ultrasound apparatus and respectively to the unit generating the electric excitation signals and to the unit evaluating the electric receipt signals. This connection takes place however at the level of the output line 31" of the preamplifier 3 of the same or corresponding transducer of the second array of transducers so that if any decoupling is necessary this can be carried out with a very simple decoupling unit which does not lead to a considerable increase in circuital complexity.

Thus in order to reduce the dimensions of the single preamplifiers and eventually of the simple decoupling unit there is no need to carry out an extreme integration and miniaturization process reducing the costs of each preamplifier.

Figure 7:
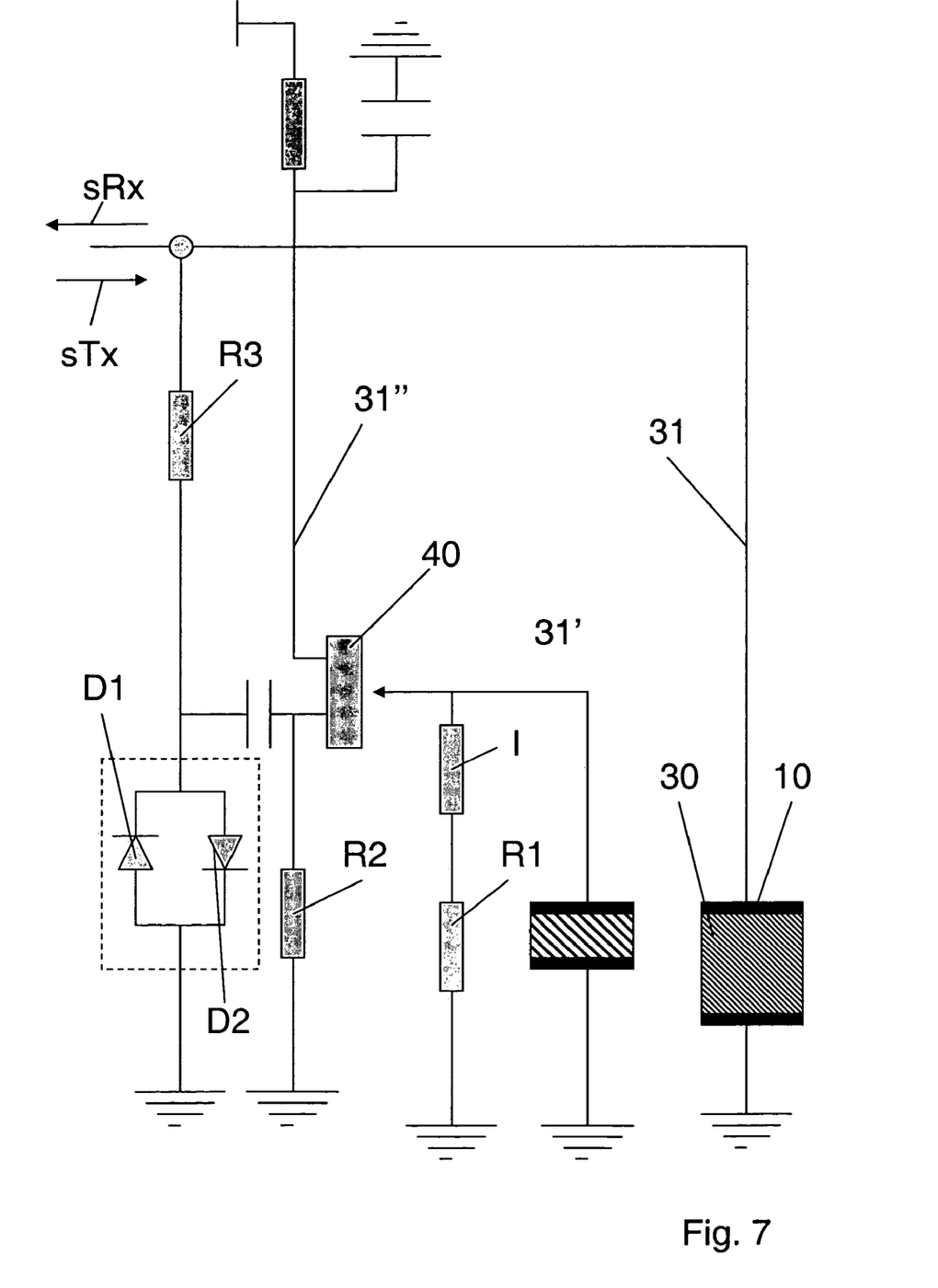
FIG. 7 is a simplified block diagram of a particular preamplifier which can be applied in combination with the probe according to one embodiment of the disclosure.

An example of a simple preamplifier and of the simple decoupling circuit associate to it is illustrated in FIG. 7. The preamplifier is formed by a FET 40 which is associated with typical elements for correctly driving such a component as an inductance I and resistance R1, resistance R2 and resistance R3. The receipt signal sRx generated by a transducer and collected by its electrode 10 is fed to the FET 40 by means of the signal feeding line 31. The FET 40 output is connected by means of an output line 31" to a conductor of a multi-channel probe connection cable. The same conductor is used for transmitting the excitation signal sTx to the transducer 30 of the first array of emitting transducers which by means of the separated feeding line 31 connects the conductor to the contact electrode 10 of the emitting transducer 30. A decoupling circuit basically formed by two diodes D1 and D2 connected in an anti-parallel way is provided for avoiding that the excitation signal sTx is fed also to the FET via its output line 31".

As it appears clearly from the above description, the preamplifier and the decoupling circuit are very simple and the number of components is very low so that no high integration has to be carried out in order to reduce the circuits to dimensions that allow the preamplifiers to be housed within the probe casing.

As it appears clearly from FIG. 4, the preamplifiers 3 can be mounted in the form of an array of preamplifiers on a printed circuit board 4.

The printed circuit board 4 is provided with conductive tracks forming each one a separate input channel to a preamplifier 3 which input channel is connectable or connected to the signal feeding line of a contact electrode of one selected transducer of the second array of receiving transducers which forms the layer 70 of the probe head. A separate output line departs from each preamplifier 3 which ends at a corresponding pin of a connector 5. The connector 5 is made of two parts; one stably connected to the output lines and the other complementary part stably connected to a multi-channel cable for connecting the probe to an ultrasound system.

The printed circuit board 4 is provided also with conductive tracks forming the channels for the excitation signals and are connected on one side to the feeding lines of the excitation signals leading each one to a contact electrode 10 of the array of contact electrodes associated with the first array of emitting transducers forming the layer 301 of the probe. The conductive tracks are connected at the opposite ends to the connector pins to which the output lines of the preamplifiers 3 are connected, which preamplifiers 3 being associated with the same or corresponding transducer of the second array of receiving transducers forming the layer 70 of the probe head.

Thus the multi-channel cable for connecting the probe to the apparatus has a common channel in form of a common conductor for each couple of corresponding transducers of the first and of the second array of transducers provided in the probe head.

As it appears from FIG. 4, the probe may be provided with two printed circuit boards each one carrying a partial array of preamplifiers 4. Furthermore the printed circuit boards may be of the kind having conductive tracks on both sides (double sided printed boards) so that a part of the total number of preamplifiers is arranged on each side of each of the printed circuit boards.

As it appears also from FIG. 4, the printed circuit boards 4 carrying the preamplifiers 3 are positioned in the probe casing along the longitudinal sides of the probe casing having the major width, since normally the probe head has essentially rectangular symmetry. According to a variant, the printed circuit boards could be positioned along three or four sides of the probe casing and extend in the direction of the longitudinal axis of the probe which normally is essentially perpendicular to the probe head. Normally the probe casing has an elongated shape in a direction perpendicular to the probe head and the part extending backwards away from the probe head forms the probe handle. The part of the casing forming the handle has normally a rounded cross section so that the printed circuit boards are placed along the sides of a parallelepipedon having a polygonal cross section which is inscribed in the rounded cross section of the part of the casing forming the handle.

Many variants of the disposition of the printed circuit boards can be chosen depending on the final shape of the probe casing and the above cited are only non-limiting examples of preferred embodiments of arranging the printed circuit boards carrying the arrays of preamplifiers 3.

What is claimed is:

1. An ultrasound probe particularly for diagnostic purposes comprising:

a first array of ultrasound transducers capable of generating ultrasound waves by electric excitation and of transforming ultrasound waves impinging on said transducers into electric signals;

each of said transducers being provided with a plurality of contact electrodes which are connected respectively to a ground potential and to conductors for transmitting or receiving an electric signal;

each of said transducers being at least electrically isolated form the adjacent surrounding ones of said transducers of said array;

said array of transducers being covered on a side formed by the ultrasound emitting surfaces of said transducers by means of at least one matching layer for adapting the acoustical impedance of said transducer array to the acoustical impedance of the body to be examined in order to avoid abrupt changes in the acoustic impedance which would generate reflection surfaces preventing said ultrasound waves from penetrating within said body to be examined;

said first array of transducers comprising transducers configured for generating and transmitting said ultrasound waves;

a second array of transducers being disposed over said first array of transducers, said second array of transducers comprising receiving transducers configured for generating electric signals due to acoustic excitation of said transducers of said second array of transducers by impinging or reflected ultrasound waves;

said second array of transducers being formed by a material having piezoelectric behaviour and an acoustic impedance intermediate to said acoustic impedance of said first array of transducers and of said body under examination, forming at the same time one of said matching layers covering said first array of transducers on a side thereof oriented in the direction of propagation of said ultrasound waves emitted by said first array of transducers.

2. An ultrasound probe according to claim 1, wherein said second array of transducers comprises receiving transducers made of Polivinilchloride PVC or polivinilidilenefluoride PVDF.

3. An ultrasound probe according to claim 1, wherein each of said transducers of said second array of transducers is provided with two electrodes, one electrode collecting electric signal generated due to acoustic excitation of said transducers of said second array of transducers by said reflected ultrasound waves, the other electrode being connected to ground potential.

4. An ultrasound probe according to claim 1, wherein said transducers of said first and second arrays of transducers are mechanically integrated in a layer-shaped pack which is formed by said transducers spaced one from the other, the spaces between said transducers being filled with a filling and bonding material.

5. An ultrasound probe according to claim 3, wherein each of said arrays of transducers is coupled to said contact and ground electrodes formed by an array of electrodes, each electrode of the array of electrodes coinciding with a surface of a corresponding one of said transducers, said array of electrodes being in the form of a layer.

6. An ultrasound probe according to claim 3, wherein said ground electrodes of said transducers are formed by a continuous layer or thin plate of conductive material connected to ground potential.

7. An ultrasound probe according to claim 1, comprising a first matching layer being provided between said first and second arrays of transducers, said second array of transducers also forming a second layer with said first array of transducers.

8. An ultrasound probe according to claim 1, wherein said second layer of transducers is made by a piezoelectric material and is formed by an array of elements having the function of ultrasound transducers, with a further layer being made by an array of contact electrodes each one of said contact electrodes coinciding and in electric contact with one of said piezoelectric elements being provided between said array of piezoelectric elements and said first matching layer, and a layer of conducting material forming said ground electrode being disposed between said second array of transducers and an acoustic lens and being in electric contact with said piezoelectric elements forming said second array of transducers.

9. An ultrasound probe according to claim 1, wherein said probe comprises a probe head for emitting and receiving ultrasound waves comprising in an order from the back side of said probe to said probe head from which said waves are emitted and at which said waves are received:
  a first layer made by an array of excitation contact electrodes which carry excitation signals separately to each one of said transducers of said first array of transducers disposed on said first layer of said excitation contact electrodes carrying said excitation signals;
  a layer of electric conductive material disposed on said first array of transducers and in electric contact with said transducers, said layer of electric conductive material being connected to ground potential and forming said ground electrodes of said first array of transducers;
  a first matching layer made of a material having a first value of acoustic impedance between the acoustic impedance of said first array of transducers and the body under examination, said first matching layer being disposed on said grounded layer of said conductive material;
  a layer made by an array of receipt contact electrodes for carrying receiving electric signals generated by said second array of transducers due to acoustic excitation of said transducers by said reflected or impinging ultrasound waves, said layer of receipt contact electrodes being disposed on said first matching layer;
  a second array of transducers disposed on said layer of receipt contact electrodes, each one of said transducers of said second array being in electric contact with one of said receipt contact electrodes of said array of receipt contact electrodes;
  said second array of transducers comprising a piezoelectric element having a value of acoustic impedance between the value of the acoustic impedance of said first matching layer and the value of the acoustic impedance of said body under examination;
  a layer of electric conductive material disposed on said second array of transducers being in electric contact with said transducers, said layer of electric conductive material connected to ground potential and forming said ground electrodes of said second array of transducers; and
  an acoustic lens being disposed over said grounded layer of electric conductive material.

10. An ultrasound probe according to claim 9, wherein each of said contact electrodes of said array of contact electrodes associated with said first array of transducers are connected to a separate feeding channel or line for an electric excitation signal and wherein each of said contact electrodes of said array of contact electrodes associated with said second array of transducers are connected to a separate feeding line or channel for the electric receipt signal, said feeding lines for said electric excitation signals and for said electric receipt signals being separate lines or channels.

11. An ultrasound probe according to claim 1, further comprising an array of preamplifiers, each one of which is connected to a separate contact electrode of one of said transducers of said second array of transducers.

12. An ultrasound probe according to claim 11, wherein said preamplifiers are in the form of integrated circuits mounted in an array disposed on a printed circuit board comprising conductive tracks, at least part of each one of said conductive tracks being a separate receipt signal feeding channel or line connecting one of said preamplifiers with said contact electrode of one of said transducers of said array of transducers.

13. An ultrasound probe according to claim 11, wherein each of said preamplifiers comprise a tension follower and passive components for driving said tension follower.

14. An ultrasound probe according to claim 13, wherein a decoupling circuit comprising two antiparallel diodes is associated with each of said tension followers.

15. An ultrasound probe according to claim 13, wherein each of said tension followers comprise a FET component.

16. An ultrasound probe according to claim 1, wherein said probe comprises at least an array of receipt signal preamplifiers mounted on a printed circuit board, said printed circuit board being housed in said probe casing in a position which is transversal or substantially perpendicular to the surface of said first and second arrays of transducers.

17. An ultrasound probe according to claim 16, wherein said preamplifiers are distributed on two arrays which are mounted each one on a side of said printed circuit board, said circuit board being double sided.

18. An ultrasound probe according to claim 16, wherein said preamplifiers are distributed on two or more arrays each mounted on one circuit board.

19. An ultrasound probe according to claim 16, wherein more than two arrays of said preamplifiers are mounted on both sides of at least two double sided printed circuit boards.

20. An ultrasound probe according to claim 1, wherein said probe has a shape with a casing having an elongated form in a direction parallel to the direction of propagation of the emitted ultrasound waves and which casing forms a handle for holding the probe having two opposite ends one of which carries the arrays of transducers and from the other of which ends a multi-channel cable departs for connecting the probe to an ultrasound system, while the one or more printed circuit boards carrying the array or the arrays of preamplifiers are positioned in the axial direction of the probe casing.

21. An ultrasound probe according to claim 20, characterised in that the printed circuit board or boards are provided parallel to the sides of the probe casing which are parallel to the longer sides of the arrays of transducers and at the end facing the arrays of transducers the printed circuit board or boards can be provided with contact termination pins of the conductive tracks provided on them or with a connector engageable and disengageable, while the array or the arrays of contact electrodes of the array or of the arrays of transducers are provided with a connector or with a contact termination pins along one or both of the said longer sides which contact termination pins or which connector is complementary to the one provided on the printed circuit board or boards in order to generate at least an electric connection by soldering together coinciding contact pins or to generate a disengageable electric and mechanical connection by means of the connectors.

22. An ultrasound probe according to claim 1, wherein a printed circuit board is provided along each side of the probe casing parallel, or tangential to three or to four or to more of the sides of the array of transducers, the arrays of contact electrodes being provided with a connector or with a contact termination pins on each of the said sides.

* * * * *